US005789640A

United States Patent [19]

Jin et al.

[11] Patent Number: 5,789,640
[45] Date of Patent: Aug. 4, 1998

[54] AROMATIC HYDROCARBONS ALKYLATION AND LIQUID-SOLID CIRCULATING FLUIDIZED BED FOR ALKYLATION

[75] Inventors: Yong Jin; Wugeng Liang; Zhanwen Wang; Zhiging Yu; Enze Min; Mingyuan He; Zhijian Da. all of Beijing. China

[73] Assignees: China Petro-Chemical Corporation; Tsinghua University; Research Institute of Petroleum Processing Sinopec. all of Beijing. China

[21] Appl. No.: 569,234

[22] PCT Filed: May 18, 1995

[86] PCT No.: PCT/CN95/00040

§ 371 Date: Apr. 29, 1996

§ 102(e) Date: Apr. 29, 1996

[87] PCT Pub. No.: WO95/32167

PCT Pub. Date: Nov. 30, 1995

[30] Foreign Application Priority Data

May 24, 1994 [CN] China .................. 94105710.0

[51] Int. Cl.$^6$ .................. C07C 2/68; C10G 35/04; F27B 15/08
[52] U.S. Cl. .................. 585/467; 585/447; 585/921; 585/925; 208/134; 422/144

[58] Field of Search .................. 585/447, 467, 585/921, 925, 446; 208/134; 422/139, 140, 144, 147

[56] References Cited

U.S. PATENT DOCUMENTS

| 5,012,021 | 4/1991 | Vora .................. 585/315 |
| 5,489,732 | 2/1996 | Zhang et al. .................. 585/467 |
| 5,565,090 | 10/1996 | Gosling et al. .................. 208/134 |

OTHER PUBLICATIONS

Vora et al.. Tenside Surfactant Detergent 28(4). 287–294 (1991).

*Primary Examiner*—Glenn Caldarola
*Assistant Examiner*—In Suk Bullock
*Attorney, Agent, or Firm*—Kane. Dalsimer. Sullivan. Kurucz, Levy, Eisele and Richard

[57] ABSTRACT

Disclosed is a process for continuous alkylation of aromatics or their derivatives in the presence of a solid acid catalyst in a liquid-solid circulating fluidized bed system, said system comprising a liquid-solid cocurrent upflow reactor, a sedimentation washing tower for the used catalyst, a liquid-solid cocurrent upflow regenerator, a sedimentation washing tower for the regenerated catalyst, and two vortical liquid-solid separators. By regeneration of the used catalyst, continuous alkylation process is achieved in this system.

13 Claims, 3 Drawing Sheets

AROMATIC HYDROCARBONS ALKYLATION AND LIQUID-SOLID CIRCULATING FLUIDIZED BED FOR ALKYLATION

FIELD OF THE INVENTION

The present invention relates to a continuous alkylation process and a liquid-solid circulating fluidized bed system for the continuous alkylation process. More specifically, the invention relates to a continuous alkylation process of aromatics or their derivatives in the presence of a solid acid catalyst and a liquid-solid circulating fluidized bed system for such a process in which the reaction of the reactants and the regeneration of the used solid acid catalyst proceed continuously.

BACKGROUND OF THE INVENTION

Alkylation reaction is one of the most important reactions in the petrochemical industry, for example, the product of the alkylation of benzene with propylene is the raw material for propanone and phenol; the alkylation of iso-butane with butene produces high octane number gasoline; and the alkylation of benzene with long chain olefins ($C_{10}$–$C_{18}$ olefins) produces the raw materials for detergents and surfactants. The previous catalysts for the above processes are liquid catalysts, for example, $H_2F$, $H_2SO_4$, $H_3PO_4$, $AlCl_3$, $ZnCl_2$, and so on. However, the use of these catalysts brings about a lot of problem such as the separation of catalyst from products, treatment of the used catalyst, corrosion to the equipment and the harm to the health of the operators. Therefore, in recent years, it is an interesting subject to develop new solid catalysts to replace the above liquid catalysts for the alkylation processes.

The solid acid catalysts which have been proposed for the alkylation process are zeolite molecular sieves, such as HX, HY, HZSM-5, USY and REHY; halogen-containing cation exchanged resins, halogen-containing superacids, superacids of $SO_4^{2-}/M_xO_y$ type, and composite oxide superacids. These solid catalysts are susceptible to deactivation due to the deposition of coke formed from the polymerization of the olefins on the catalyst surface , hence, the activity of these catalysts will decrease quickly, especially, for the catalyst with high activity. This means that the solid catalysts will be run only with a very low activity during the process if no special treatment is given to these used catalysts. Although different techniques, such as the introduction of the Group VIII elements or the rare earth elements into the catalyst, have been used to prevent coke deposition on the catalyst and to improve the service life of the catalysts, the results are not satisfactory.

Another approach to the problem is to develop a new process, in which the coke deposited catalyst are regenerated timely. To satisfy the requirement of the process wherein the alkylation reaction in the presence of a solid catalyst and the regeneration of the used solid catalyst (referred to as reaction-regeneration cycle hereafter) occur alternatively, it is critical to develop new process equipment in which the above process can be realized (Vora, B. V. et al., Tenside Surfactant Detergent, 28(4), 287–294, 1991). It has been reported that the fixed bed and continuously stirred batch reactors have been used for such a process.

In the fixed bed reactor, when the activity of the catalyst decreases to a certain level, the reactor will be switched to regeneration phase. The regeneration proceeds in the same reactor by changing the reactants into regenerating reagent. After the coke deposited on the catalyst surface is removed by the regenerating reagent, the reactor will be switched to reaction phase again. By this way, the reaction-regeneration cycle advances alternately and the process proceeds continuously. A pilot process based upon the above philosophy has been developed by UOP (U.S. Pat. No. 5,012,021). Because there is a time interval between reaction and regeneration phase, there should be 3 or more reactors for total process.

The situation of the continuously stirred batch reactor is the same as that of the fixed bed reactor. The fresh solid catalyst contacts the reactants in the reactor and reaction undergoes in it. When the activity of the catalyst decreases to a certain level, the reactants and products are withdrawn out of the reactor, while the catalyst remains within the reactor. Subsequently, the regenerating reagent is introduced into the reactor and the catalyst is regenerated. After that, the reactor is switched to reaction phase again, and this process proceeds repeatedly.

In summary, all the prior art reaction-regeneration cycle undergoing either in the fixed bed reactor or in the continuously stirred batch reactor, are in a batch mode, the reaction period depends on the deactivation rate constants of the catalyst. For the catalyst susceptible to deactivation, frequent switching brings about the following disadvantages: overelaborate operation, huge investment cost, unnecessary loss of reactants and regenerating reagent when the switching is undertaken, the low production efficiency under batch operation, and the most important, the decreasing activity or even very low activity of the catalyst throughout the reaction.

It is, therefore, an object of the present invention to provide a process for continuous alkylation of aromatics or their derivatives in the presence of a solid acid catalyst, wherein the reaction-regeneration cycle takes place continuously.

Another object of the present invention is to provide a liquid-solid circulating fluidized bed system in which continuous alkylation is carried out.

SUMMARY OF THE INVENTION

The process for continuous alkylation of aromatics or their derivatives provided by the present invention is shown in FIG. 1, which comprises (a) contacting the reactants with a solid acid catalyst in a liquid-solid concurrent upflow reactor (1);

(b) passing the liquid-solid mixture consisting of used solid acid catalyst and the unreacted reactants and the products into a vortical liquid-solid separator (2) to give separated used solid acid catalyst;

(c) passing said separated used solid acid catalyst through a sedimentation washing tower (3) into a liquid-solid concurrent upflow regenerator (4);

(d) contacting said separated used solid acid catalyst in said regenerator (4) with the regenerating reagent which is a reactant selected from the group comprising aromatics and their derivatives;

(e) passing the liquid-solid mixture consisting of the regenerated catalyst and the regenerating reagent into a vortical liquid-solid separator (5) to give separated regenerated solid acid catalyst; and (f) returning the separated regenerated solid acid catalyst to a sedimentation washing tower (6), then into said reactor (1). Thus, the reaction-regeneration cycle is carried out continuously.

The structure of the liquid-solid circulating fluidized bed system provided by the present invention suitable for the continuous alkylation process according to the present invention is shown in FIG. 1, which comprises a liquid-solid concurrent upflow reactor (1), a sedimentation washing tower (3) for the used catalyst, a liquid-solid concurrent upflow regenerator (4), a sedimentation washing tower (6) for the regenerated catalyst, and two vortical liquid-solid separator (2) and (5), wherein the top of said reactor (1), which has two inlets (7) and (8) for reactants, connects with said vortical liquid-solid separator (2), which in turn connects with the top of said sedimentation washing tower (3), and the bottom of said reactor (1) connects with the bottom of sedimentation washing tower (6), and wherein the top of said regenerator (4), which has two inlets (11) and (12) for regenerating reagent and is set up parallel to said reactor (1), connects with said vortical liquid-solid separator (5), which in turn connects with the top of said sedimentation washing tower (6), and the bottom of said regenerator (4) connects with the bottom of said sedimentation washing tower (3).

BRIEF DESCRIPTION OF DRAWINGS

For a more complete description of the continuous alkylation process of this invention, reference shall be made to the accompanying figures illustrating the present continuous liquid-solid circulating fluidized bed system, wherein.

DETAILED DESCRIPTION OF THE INVENTION

As used herein, the term "liquid-solid concurrent upflow reactor/ regenerator" refers to a column set up vertically, in which the liquid (e.g. the reactants or regenerating reagent) and the solid (e.g. the solid acid catalyst) move upwards concurrently, they can be any known column suitable for such a reaction or regeneration.

As used herein, the term "sedimentation washing tower" refers to a tower in which the solid acid catalyst, while settling, are washed by the liquid moving upwards.

As used herein, the term "liquid-solid vortical separator" refers to a separator, and the mixture consisting of solid acid catalyst and liquid enters into it in the tangent direction and are separated from each other in it.

As used herein, the term "opening ratio" refers to the ratio of the pore area of a plate to the total area of the plate.

As used herein, the term "voidage" refers to the ratio of the volume of the liquid contained in a column to the total volume of the same column, with the volume of liquid and solid, if any, contained in a column equal to the volume of the same column.

Figure 1:
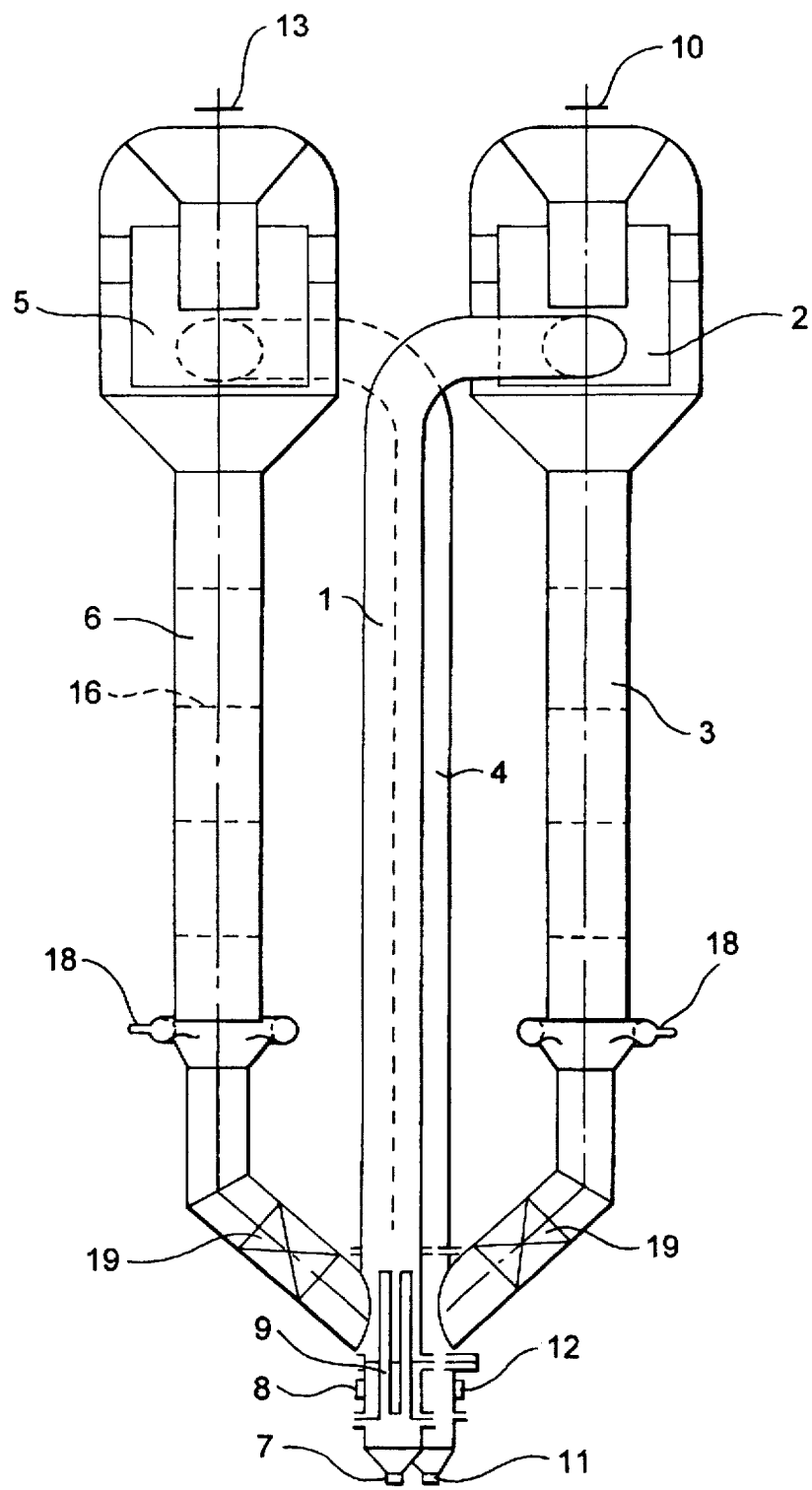
FIG. 1 represents the continuous alkylation process according to the invention and the schematic apparatus of the continuous liquid-solid circulating fluidized bed system.

The process for continuous alkylation of aromatics or their derivatives provided by the present invention is shown in FIG. 1. The reactants provided according to the required ratio of reactants and mixed well are divided into two parts, one part is pumped by a metering pump into the reactor 1 via the first inlet 7, and the other is pumped into the reactor 1 via the second inlet 8; the reactants which get into the reactor via the first inlet 7 are used to bring the solid acid catalyst particles to a circulating fluidized state, while the reactants which go into the reactor via the second inlet 8 are use to change the resistance to catalyst particles at the inlet, hence to regulate the catalyst circulation rate. After passing through the combined distributor 9, the reactants enter into the concurrent upflow reactor 1. In reactor 1, the reactants get into contact with the solid acid catalyst of a diameter of 0.05–0.8 mm, and the alkylation reaction takes place. The flow rates of reactants and catalyst are maintained in such a way as to keep a voidage of the reactor of 0.68–0.95. Under the operating conditions of a temperature of 0°–350° C. and a pressure of 1–30 atm, the catalyst is transported by the reactants and products from the bottom to the top of the reactor, with the liquid flow rate being 1–15 times the terminal settling velocity of the catalyst particles, at last the liquid and solid mixture leaves the reactor and enters into the vortical liquid-solid separator 2 in the tangent direction at a liquid flow rate of 1–10 m/s. The separated liquid products (which contains very little unconverted reactants) get into the product reservoir from the product outlet 10, while the used catalyst particles enters into the sedimentation washing tower 3. In the sedimentation washing tower 3, the used catalyst particles gets into contact with the washing reagent which is the same as the reactant(s) selected from the group comprising aromatics and their derivatives, and the washing reagent moves upwards in the tower at a flow rate 0.5–5 times the terminal settling velocity of the catalyst particles and takes away the product and some coke deposits formed on the catalyst surface, then, the used catalyst particles enter into the concurrent upflow regenerator 4, the regenerating reagent which is a reactant selected from the group comprising aromatics and their derivatives is divided into two parts, one part is pumped by a metering pump into the regenerator 4 via the first inlet 11, and the other is pumped into the regenerator 4 via the second inlet 12; the regenerating reagent which gets into the regenerator 4 via the first inlet 11 is used to bring the used catalyst particles to a circulating fluidized state, while the regenerating reagent which goes into the regenerator 4 via the second inlet 12 is used to change the resistance to used catalyst particles at the inlet, hence to regulate the circulation rate of the used catalyst. After passing through the combined distributor 9, the regenerating reagent enters into the concurrent upflow regenerator 4. In the regenerator 4, the regenerating reagent contacts the used solid acid catalyst and removes the coke deposited on it. The flow rates of regenerating reagent and the used catalyst are maintained in such a way as to keep a voidage of the regenerator 4 of 0.68–0.95. Under the operating conditions of a temperature of 70°–450° C. and a pressure of 1–25 atm, the used catalyst is transported by the regenerating reagent from the bottom to the top of the regenerator 4, with the liquid flow rate being 1–15 times the terminal velocity of the used catalyst particles, at last the liquid and solid mixture leaves the reactor and enters into the vortical liquid-solid separator 5 in the tangent direction at a liquid flow rate of 1–10 m/s. The separated regenerating reagent goes into the regenerating reagent reservoir from the regenerating reagent outlet 13, while the regenerated catalyst particles enters into sedimentation washing tower 6. In the sedimentation washing tower 6, the regenerated catalyst contacts the washing reagent which is the same as the reactant(s) selected from the group comprising aromatics and their derivatives, while the washing reagent moves upwards in the tower at a velocity 0.5–5 times the terminal settling velocity of the regenerated catalyst particles and further takes away the coke deposits and remaining washing reagent on it, at last, the regenerated catalyst particles enter into the concurrent upflow reactor 1, thus a reaction-regeneration cycle is finished. By repeating such a reaction-regeneration cycle a continuous alkylation process with a high catalyst activity is attained.

The continuous alkylation process provided by the present invention realizes the alkylation reaction in the presence of a solid acid catalyst in a continuous manner and due to the fact that the reaction-regeneration cycle is operated under circulating fluidization, the catalyst can be ensured to be of high activity. Such a alkylation can be, for example, the alkylation of aromatics or their derivatives with olefins with 2–20 carbon atoms in the presence of various types of solid acid catalyst. In the process of the present invention, the reactants and regenerating reagent get into the system by two paths, moreover, the flow rates of the two parts can be regulated respectively, hence, both the reaction conversion and the regenerating efficiency can be controlled. In the present process, because the regenerating reagent and the washing reagent are the same aromatic or its derivatives as the reactants, the process is simplified by eliminating a subsequent separation step and by eliminating pollution of the reactants by the regenerating reagent other than the reactants.

The present invention can also be used in other similar heterogeneous catalytic reaction systems provided that the reactants or the products can be used to remove the coke or other pollutants deposited on the catalyst, for example, the alkylation of iso-paraffine with butene to give the high octane number gasoline can be carried out under 10–30 atm and 0°–100° C. with TMP (trimethyl pentane) used as the regenerating reagent.

Figure 2:
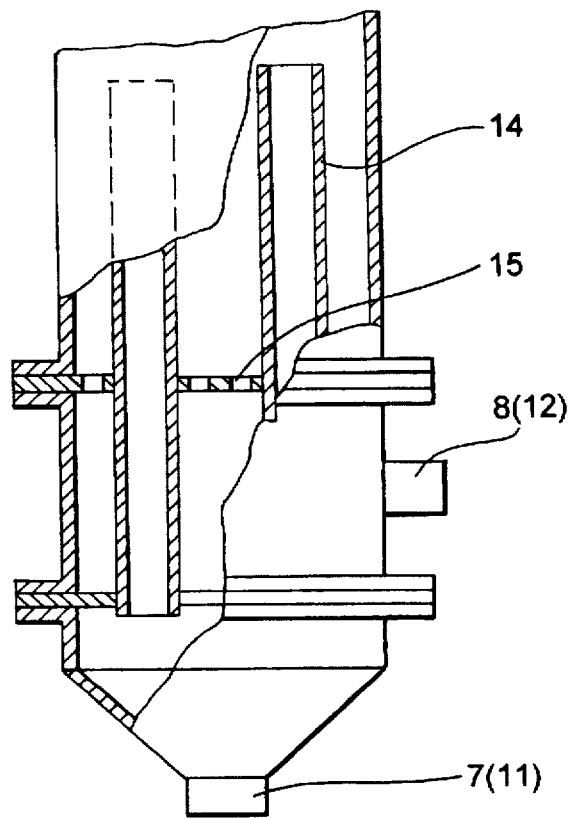
FIG. 2 represents the schematic apparatus of the combined distributors installed in the reactor and regeneratator.
Figure 3:
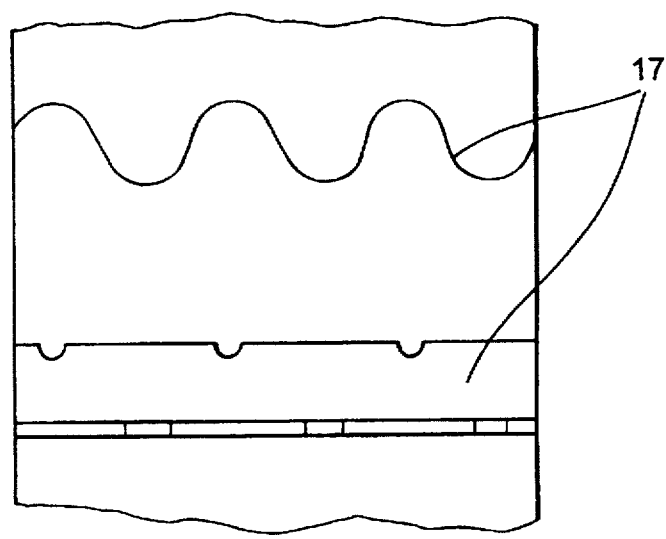
FIG. 3 represents the structure of internals installed in the sedimentation washing tower.

The liquid-solid circulating fluidized bed system suitable for the continuous alkylation process according to the invention is shown in FIG. 1, which mainly comprises six parts: a liquid-solid concurrent upflow reactor 1, a sedimentation washing tower 3 for the used catalyst, a liquid-solid concurrent upflow regenerator 4, a sedimentation washing tower 6 for the regenerated catalyst, and two vortical liquid-solid separators 2 and 5. The six parts are set up vertically with said liquid-solid concurrent upflow reactor 1 parallel to said liquid-solid concurrent upflow regenerator 4, said sedimentation washing tower 3 parallel to said sedimentation washing tower 6, and said vortical liquid-solid separator 2 parallel to said vortical liquid-solid separator 5. The top of said liquid-solid concurrent upflow reactor 1 connects with said vortical liquid-solid separator 2, which in turn connects with the top of said sedimentation washing tower 3, while the bottom of said liquid-solid concurrent upflow reactor 1 connects with the bottom of said sedimentation washing tower 6, and the top of said liquid-solid concurrent upflow regenerator 4 connects with said vortical liquid-solid separator 5, which in turn connects with the top of said sedimentation washing tower 6, while the top of said liquid-solid concurrent upflow regenerator 4 connects with the bottom of said sedimentation washing tower 3. The liquid-solid concurrent upflow reactor 1 or regenerator 4 has two inlets 7 and 8 for reactants or 11 and 12 for regenerating reagent, and has a combined distributor 9 to connect the two inlets, which is composed of the multi-tube distributor 14 and the porous plate distributor 15, as shown in FIG. 2. The multi-tube distributor has an opening ratio of 2–15% and the porous distributor has an opening ratio of 0.5–5%. The raw materials get into the reactor or the regenerator via the two inlets and pass through the tubes or the outside of the tubes of the combined distributor. In the sedimentation washing tower 3 and 6, there are the combined internals 16 to increase the interaction between the liquid and solid phases. The inter-nals is made up of the corrugated plate 17, which is shown in FIG. 3. Besides the corrugated plate, other baffler such as the plate baffler or the pagoda type baffler, can also be used. There are pores at the wavecrest portions and the wave valley portions of the corrugated plate, which is provided for the liquid and solid to pass through, with the diameter of the pore being 1/20–1/50 of the diameter of the washing tower, and the opening ratio being 10–40%. The corrugated plates are horizontally mounted with wave valley thereof at an angle of 90° to the wave valley of the corrugated plate thereover and/or thereunder. At the bottom of the sedimentation washing tower 3 or 6, there is a liquid inlet 18 for the regenerating reagent or the washing reagent. There is a valve 19 on the joint position between the bottoms of sedimentation washing tower and the reactor or the regenerator.

The liquid-solid circulating fluidized bed system provided by the present invention can realize the continuous alkylation process in the presence of a solid acid catalyst and can ensure the operation with a high activity of the catalyst. Because the liquid and solid phases are in a plug flow, the reaction or regeneration gives high conversion or efficiency and the temperature of the systems is distributed uniformly in axial direction and easy to control. There are two inlets at the bottoms of the reactor and regenerator, so the conversion in the reactor and the regenerating efficiency in the regenerator can be controlled by regulating the flow rates via the inlets. The vortical liquid-solid separator is chosen for the present system because the centrifugal force provided by the structure of such a separator enables the liquid and solid mixture entering in the tangent direction to be separated from each other at a high speed in high efficiency. Because the combined internals, especially the corrugated plate, is installed in the sedimentation washing tower, the contact between the washing reagent and the solid catalyst is highly efficient and the washing is highly effective, thus the catalyst with a clean active surface is provided for the reactor.

PREFERRED EMBODIMENT OF THE INVENTION

The following examples are provided to illustrate the invention and its advantages more clearly, but the present invention is not restricted to these examples.

EXAMPLE 1

Example 1 illustrates that the process of the present invention can keep high conversion of the reactants under long time continuous operation.

The dodecene and benzene undergo alkylation in the presence of a supported HY zeolite catalyst by the process shown in FIG. 1. The inner diameter of the reactor and the regenerator are the same, and the ratio of height to diameter is 10:1, with the reaction temperature being 110–120° C., the regeneration temperature being 165–175° C., the pressure within the reactor or the regenerator being 4.5–6.0 atm, and the flow rates of the reactants or the regenerating reagent being 10 liter/hour respectively, the conversion of dodecene at the outlet of the reactor are kept at 99.5% throughout the 200 hours continuous operation.

Table 1 shows the product distributions of the linear alkylbenzene of the alkylation with HF catalyst and HY catalyst by the present process. The results in Table 1 indicate that the product by the present process has a higher yield of 2-phenyldodecane and 3- phenyldodecane than by HF catalyst process. The high content of 2- phenyldodecane in the product will increase the biodegradability of the final detergent and the high content of 3-phenyldodecane in the product will increase the detersive efficiency of the final detergent, which means that the product distribution by the present process has distinguished characteristics.

TABLE 1

Comparison of the product distribution by different processes

|  | 2-P | 3-P | 4-P | 5-P | 6-P |
| --- | --- | --- | --- | --- | --- |
| HF Process | 20 | 17 | 16 | 23 | 24 |
| Present Invention | 50 | 24 | 13 | 8 | 5 |

EXAMPLE 2

This example illustrates that the liquid-solid circulating fluidized bed system of the present invention makes the catalyst display higher activity than the continuously stirred batch reactor does.

Figure 4:
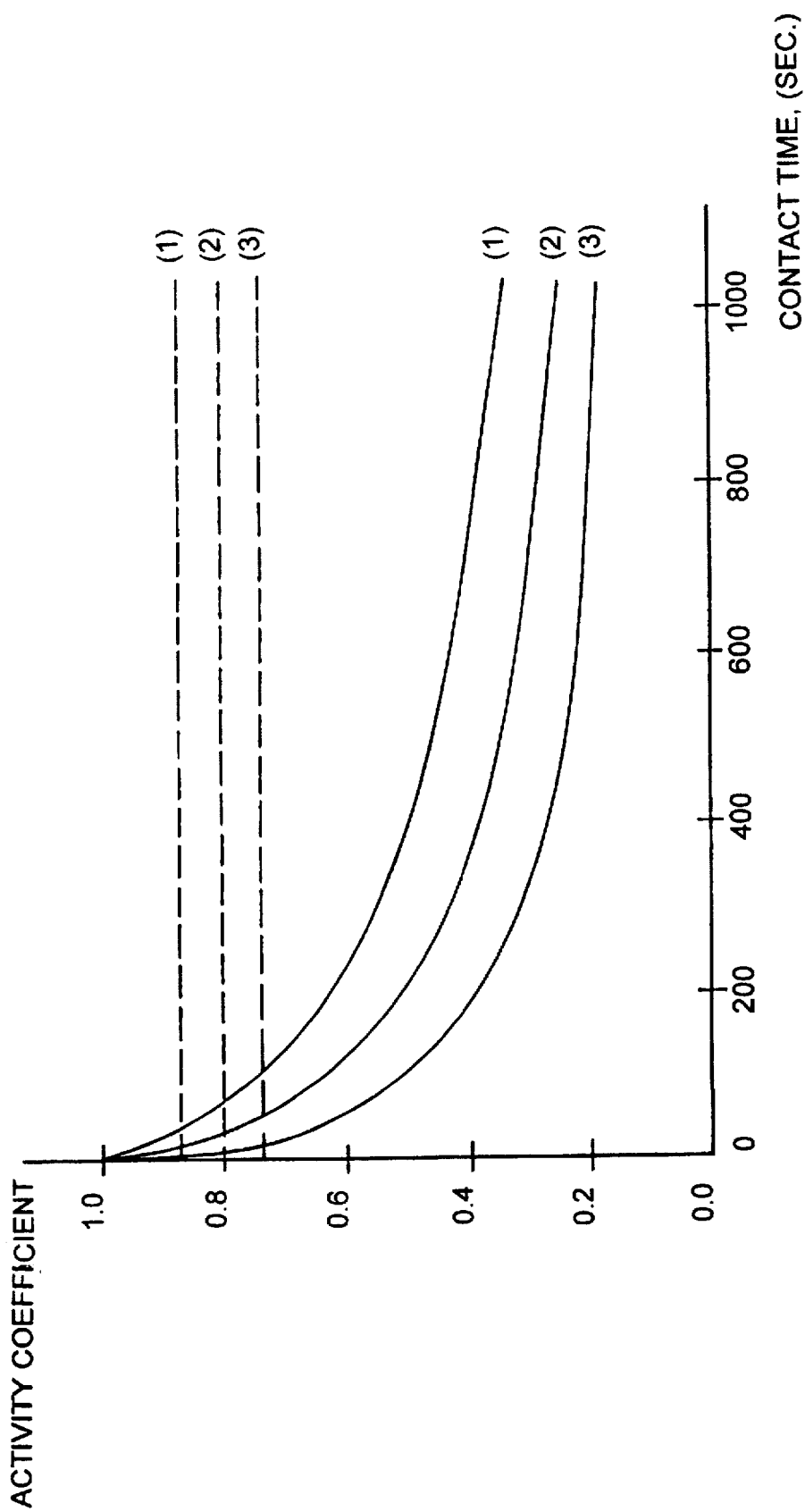
FIG. 4 represents the comparison of the activity of the catalyst obtained in the liquid-solid circulating fluidized bed system and in continuously stirred batch reactor.

The dodecene and benzene undergo alkylation in the presence of a supported HY zeolite catalyst in the liquid-solid circulating fluidized bed system and the continuously stirred batch reactor respectively under a pressure of 3 atm, the results are shown in FIG. 4, where the solid line represents the activity of catalyst in the continuously stirred batch reactor, while the dotted line represents the activity of catalyst in the liquid-solid circulating fluidized bed system, the curves (1), (2) and (3) corresponds to the reaction temperatures of 70° C., 80° C. and 90° C. respectively.

It can be seen that although the activity of the catalyst in the continuously stirred batch reactor is some higher at the beginning of the reaction, the activity of catalyst decreases very quickly; on the other hand, the initial activity coefficient of catalyst in the circulating fluidized bed system is about 0.8 while the activity is kept at this value for long time operation.

What is claimed is:

1. A process for continuous alkylation of aromatics in the presence of a solid acid catalyst, comprising
   (a) contacting the reactants with a solid acid catalyst in a liquid-solid concurrent upflow reactor (1);
   (b) passing the liquid-solid mixture consisting of used solid acid catalyst and the unreacted reactants and the products into a vortical liquid-solid separator (2) to give separated used solid acid catalyst;
   (c) passing said separated used solid acid catalyst through a sedimentation washing tower (3) into a liquid-solid concurrent upflow regenerator (4);
   (d) contacting said separated used solid acid catalyst in said regenerator (4) with the regenerating reagent which is a reactant selected from the group comprising aromatics;
   (e) passing the liquid-solid mixture consisting of the regenerated catalyst and the regenerating reagent into a vortical liquid-solid separator (5) to give separated regenerated solid acid catalyst; and
   (f) returning the separated regenerated solid acid catalyst to a sedimentation washing tower (6), then into said reactor (1).

2. A process of claim 1, wherein said solid acid catalyst is solid particles of a diameter of 0.05–0.8 mm, which are transported by the reactants and the products or the regenerating reagents from the bottom to the top of said reactor (1) or said regenerator (4) with the liquid flow rate being 1–15 times the terminal settling velocity of the solid acid catalyst, and the total flow rate of said solid acid catalyst, and the reactants and products or the regenerating reagent being such that the voidage of the fluidized bed is 0.68–0.95, and wherein the used or regenerated solid acid catalyst together with the unreacted reactants and the products or the regenerating reagent enters into said vortical liquid-solid separator (2) or (5) in the tangent direction at a liquid flow rate of 1–10 m/s.

3. A process of claim 1, wherein the contact between the solid acid catalyst and the reactants is carried out at a temperature of 0°–350° C. and a pressure of 1–30 atm.

4. A process of claim 1, wherein the contact between the used solid acid catalyst and the regenerating reagent is carried out at a temperature of 70°–450°C. and a pressure of 1–25 atm.

5. A process of claim 1, wherein the reactants enters into the reactor (1) via the first inlet (7) and the second inlet (8).

6. A process of claim 1, wherein the regenerating reagent enters into the regenerator (4) via the first inlet (11) and the second inlet (12).

7. A process of claim 1, wherein the separated used solid acid catalyst is contacted with the washing reagent in the sedimentation washing tower (3) with the washing reagent moving upward in the tower (3) at a velocity 0.5–5 times the terminal settling velocity of the used solid acid catalyst.

8. A process of claim 7, wherein the washing reagent is the same as the regenerating reagent, which is a reactant selected from the group comprising aromatics.

9. A process of claim 1, wherein the regenerated solid acid catalyst is contacted with the washing reagent in the sedimentation washing tower (6) with the washing reagent moving upward in the sedimentation washing tower (6) at a velocity 0.5–5 times the terminal settling velocity of the solid acid catalyst.

10. A process of claim 9, wherein the washing reagent is the same as the regenerating reagent, which is a reactant selected from the group comprising aromatics and their derivatives.

11. A liquid-solid circulating fluidized bed system for the process of claim 1, which comprises a liquid-solid concurrent upflow reactor (1), a sedimentation washing tower (3) for the used catalyst, a liquid-solid concurrent upflow regenerator (4), a sedimentation washing tower (6) for the regenerated catalyst, and two vortical liquid-solid separator (2) and (5), wherein the top of said reactor (1), which has two inlets (7) and (8) for reactants, connects with said vortical liquid-solid separator (2), which in turn connects with the top of said sedimentation washing tower (3), and the bottom of said reactor (1) connects with the bottom of sedimentation washing tower (6), and wherein the top of said regenerator (4), which has two inlets (11) and (12) for regenerating reagent and is set up parallel to said reactor (1), connects with said vortical liquid-solid separator (5), which in turn connects with the top of said sedimentation washing tower (6), and the bottom of said regenerator (4) connects with the bottom of said sedimentation washing tower (3).

12. A system of claim 11, wherein connecting the two inlets of said reactor (1) and said regenerator (4) is a combined distributor (9) respectively, which is composed of a multi-tube distributor (14) with an opening ratio of 2–15% and a porous plate distributor (15) with an opening ratio of 0.5–5%.

13. A system of claim 11, wherein in the sedimentation washing towers (3) and (6), there are provided combined internals (16) composed of corrugated plate (17) with an opening ratio of 10–40% and with pores at its wavecrest portions and wave valley portions, and wherein said corrugated plate (17) are horizontally mounted with the wave valley thereof at an angle of 90° to the wave valley of the corrugated plate thereover and/or thereunder.

* * * * *